US009220656B2

(12) United States Patent
Rosenberg

(10) Patent No.: US 9,220,656 B2
(45) Date of Patent: Dec. 29, 2015

(54) METHOD AND APARATUS FOR ARTIFICIAL INSEMINATION

(71) Applicant: Doron Rosenberg, Toronto (CA)

(72) Inventor: Doron Rosenberg, Toronto (CA)

( * ) Notice: Subject to any disclaimer, the term of this patent is extended or adjusted under 35 U.S.C. 154(b) by 161 days.

(21) Appl. No.: 14/052,134

(22) Filed: Oct. 11, 2013

(65) Prior Publication Data

US 2014/0107410 A1    Apr. 17, 2014

Related U.S. Application Data

(60) Provisional application No. 61/714,755, filed on Oct. 17, 2012.

(51) Int. Cl.
| | |
|---|---|
| *A61B 17/43* | (2006.01) |
| *A61H 19/00* | (2006.01) |
| *A61H 23/00* | (2006.01) |
| *A61H 23/02* | (2006.01) |
| *A61H 35/00* | (2006.01) |
| *A61B 17/00* | (2006.01) |

(52) U.S. Cl.
CPC ............... *A61H 19/44* (2013.01); *A61B 17/43* (2013.01); *A61H 19/50* (2013.01); *A61H 23/00* (2013.01); *A61B 2017/00398* (2013.01); *A61B 2017/00734* (2013.01); *A61H 23/0254* (2013.01); *A61H 35/00* (2013.01); *A61H 2201/0153* (2013.01); *A61H 2201/10* (2013.01)

(58) Field of Classification Search
CPC ..... A61H 19/00; A61H 19/02; A61H 19/027; A61H 19/44; A61H 2201/105; A61H 2201/1253; A61B 17/425; A61B 17/43
USPC .......................................... 600/38–41, 33–35
See application file for complete search history.

(56) References Cited

U.S. PATENT DOCUMENTS

| 3,910,275 | A | 10/1975 | Babey et al. |
|---|---|---|---|
| 2008/0065187 | A1 | 3/2008 | Squicciarini |
| 2011/0224482 | A1 | 9/2011 | McCarthy et al. |
| 2012/0310040 | A1 | 12/2012 | Bollinger |
| 2013/0324792 | A1* | 12/2013 | Mizrahi et al. ................. 600/38 |
| 2014/0200400 | A1* | 7/2014 | Berman .......................... 600/38 |

FOREIGN PATENT DOCUMENTS

WO    WO 2005/099366 A2    10/2005

* cited by examiner

*Primary Examiner* — John Lacyk
(74) *Attorney, Agent, or Firm* — Nasser Ashgriz; UIPatent Inc.

(57) ABSTRACT

The object of the invention is to provide a device and means for artificial insemination. The present invention provides two methods of sperm delivery that aim to increase the success of intracervical artificial insemination. The shape and design of the present invention also allows artificial insemination to be a pleasurable experience.

12 Claims, 5 Drawing Sheets

METHOD AND APARATUS FOR ARTIFICIAL INSEMINATION

RELATED APPLICATIONS

This application claims the benefit under 35 U.S.C. 119(e) of U.S. Provisional Patent Application Ser. No. 61/714,755 filed Oct. 17, 2012, which is incorporated herein by reference in its entirety and made a part hereof.

FIELD OF THE INVENTION

The present invention is related to artificial insemination and more specifically to a device and method that functions for fertilization as well as pleasure.

BACKGROUND OF THE INVENTION

The present invention concerns a method for sexual partners or individuals wishing to artificially inseminate. The present invention allows female same-sex partners and choice mothers to become pregnant using donor sperm as well as aiding heterosexual couples in achieving fertility. Artificial insemination (AI) can be performed in a clinic or at home using a variety of techniques. Intracervical insemination (ICI) is the method for the deposition of fresh or frozen sperm into the cervix. Generally, in order to achieve the best success with each treatment the AI and ICI procedures are performed at a medical clinic and by medical professionals. Undergoing such procedures can lead to stress in both partners and may result in an unpleasant experience to some.

The advantages of using an ICI device as opposed to other methods of AI are that it does not require sperm "washing"—the separation of sperm from the seminal fluid—it is a relatively short procedure, and it is painless. Other methods of fertilization such as intrauterine insemination, in vitro fertilization, and surrogacy are much more costly and/or are to be performed by physicians. ICI may be performed at home with the aid of a partner or alone as long as there is a sperm donor. ICI is also not as expensive as the above physician-performed methods.

The success of a single type of fertility treatment, whether ICI or otherwise, may be dependent on a number of factors. Two factors that have not been addressed in the prior art are ensuring the accurate delivery of a large of sperm cells that to the correct position on the cervix, and the ability of female orgasm or female sexual pleasure to increase the sperm uptake into the uterus and thus increase the probability of fertilization.

ICI systems and methods are widespread and are characterized by their accessibility and lower difficulty level. Previous patents such as U.S. Pat. No. 6,511,415 and U.S. Pat. No. 8,323,178 have focused solely on delivery of sperm in the vaginal canal without considering the potential pleasurable aspects of the act. Considering some couples may that feel some form of intimacy may be lost when attempting the procedure at a clinic or using devices which resemble surgical devices it may be more preferable to provide a device that provides some pleasurable aspects during the procedure.

U.S. application Ser. No. 12/721,094 discloses a sexual device that will allow the wearer to artificially inseminate a partner and the device can be used to provide pleasure during its use. However, sperm delivery is accomplished using only a syringe that is activated by the user. This method of delivery by laypersons not trained in the method of AI may likely lead to incorrect delivery of the sperm. During ICI sperm must be delivered onto the cervix with a precise force that allows the sperm to reach the surface of the cervix during expulsion, however, the force should not be such that it results in sperm being reflected of the walls of the cervix. Additionally, too small of a volume of sperm delivered can cause back flow out of the cervical canal which may result in insufficient insemination. In order to increase the success of fertility it is most important to regulate the flow of sperm toward the cervical canal.

Devices and methods that are used in ICI require a physician to visually identify the cervix by the use of a speculum and then begin the release of sperm from the device. For best results, visual contact with the cervix has to be made throughout the procedure. Personal or home ICI kits such as described in U.S. application Ser. No. 12/721,094 do not disclose methods for ensuring the delivery of sperm to the cervix and only provide methods and devices for depositing in the vaginal canal. For these reasons it is difficult for an at home ICI device to be as successful as ICI treatments performed at a clinic by medically trained professionals.

The present invention includes methods for achieving greater success with fertility. Thus, the invention is comprised of a means for ejecting the sperm at a specific velocity so that it ensures a means of best delivery to the cervix. The present invention also includes methods that can cause pleasurable feelings. With the addition of pleasurable feelings to the user, the present invention can aid in the induction of a female orgasm and thereby potentially increase the likelihood of fertilization.

SUMMARY OF THE INVENTION

The present invention aims to provide an effective solution for couples with fertility problems, same-sex couples or other persons such as choice mothers wishing to conceive a baby by ICI while also deriving sexual pleasure in the process. Additionally, the current invention also aims to increase the success of current conventional home based ICI methods.

The first objective of the present invention is to provide a device and method for the delivery of sperm to the cervix. As such, the present invention is comprised of an inner tube that allows sperm to be expelled from a capsule somewhere in the body of the device to an opening at the distal end and out of the device. The syringe stores sperm or any other type of liquid until the time the user determines when it is ready to be expelled. The sperm or liquid container may also be a conception cap or another type of capsule that is able to store sperm.

The second objective of the present invention is to provide a more reliable method of sperm entry into the cervical canal and consequently to the uterus. The present invention comprises of a syringe pump mechanism to deliver a steady jet of sperm to the cervix. This method of delivery ensures that relatively few sperm do not arrive at the intended target.

The third objective of the invention is to provide a sperm delivery method that is pleasurable to the recipient. For this purpose, the present invention is shaped like a dildo. A dildo is a sexual device that structurally may resemble a penis, and is a device that can be used by people of all genders and sexual orientation. Insertion of the said device may resemble sexual intercourse and may result in pleasurable sensations for the recipient. The present invention is also capable of being attached to a harness as well as providing other ways of attachment during its use.

An additional feature of the invention that can be used to provide pleasure is its vibrating function. The female orgasm has been shown to result in increased ability of the uterus to uptake sperm deposited in the vagina, thus increasing the probability of fertility.

The objects features and effects of the invention are described in details below with accompanied drawings and embodiments.

The aforementioned objects of the present invention are attained by a device and method that functions for fertilization. Other objects, advantages and novel features of the present invention will become readily apparent from the following drawings and detailed description of preferred embodiments.

BRIEF DESCRIPTION OF THE DRAWINGS

Embodiments herein will hereinafter be described in conjunction with the appended photos provided to illustrate and not to limit the scope of the claims, wherein like designations denote like elements, and in which:

DETAILED DESCRIPTION OF THE PREFERRED EMBODIMENTS

The present invention and the various features and advantages details thereof are explained more fully with reference to the non-limiting embodiments described in detail in the following description.

Figure 1:
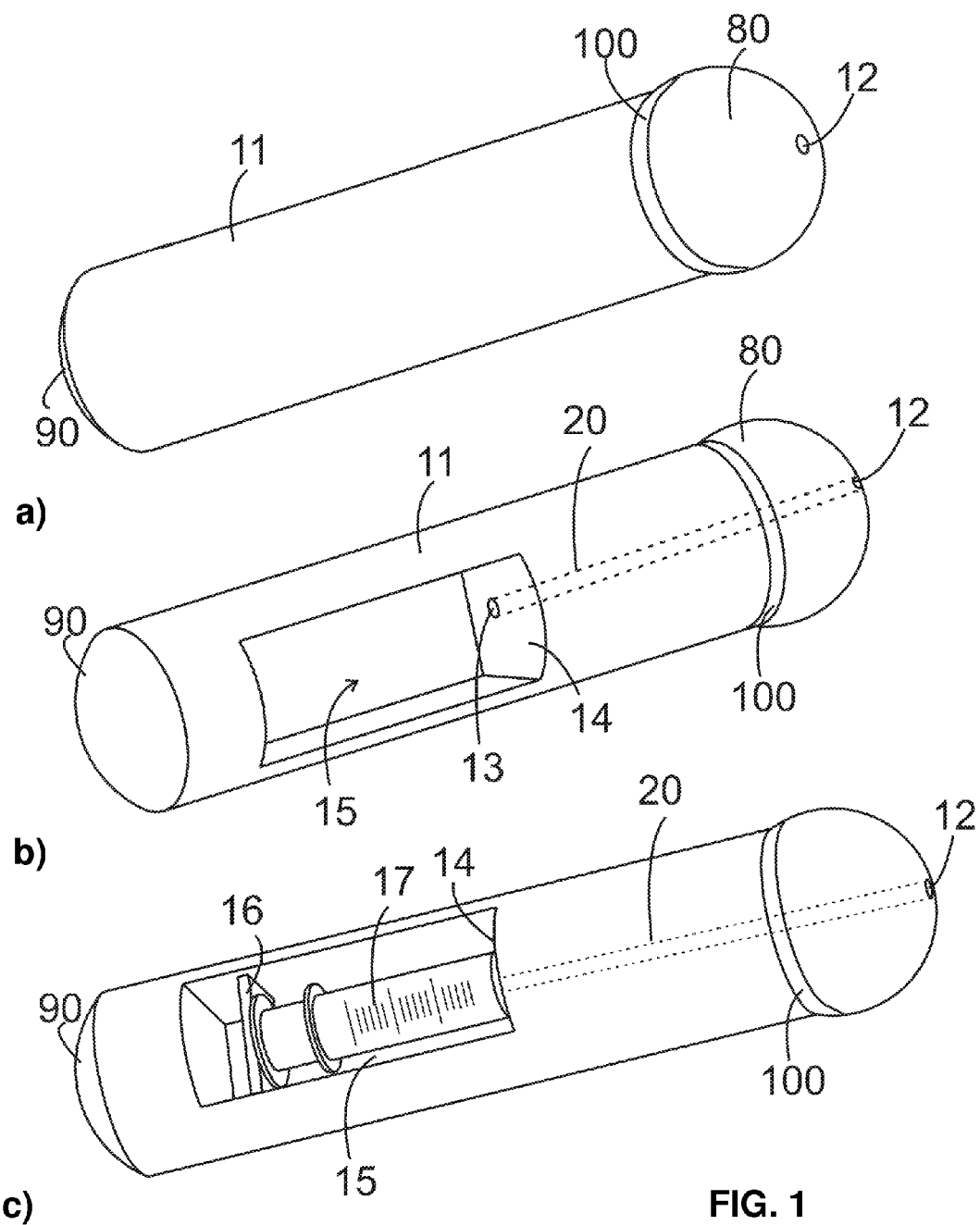
FIG. 1 shows the isometric views of the device.

FIG. 1A shows the invention consists of a dildo 11, a cylindrical tube 20, a syringe 17 and a means of sperm delivery. The device can be defined as having a proximal end 90 and a distal end 80. The dildo 11 in the present invention can be made of silicone or metal, glass, plastic, gel, or rubber which may be in the form of a penis. The dildo 11 may be a simple cylindrical shape, a penis-like shape or another shape that can be used to provide pleasure. The size of the dildo can vary based on user preference. The dildo 11 has an opening 12 at its distal end 80 which is the where sperm or any type of liquid is ejected. As shown in FIG. 1B, the dildo 11 will contain a cylindrical tube 20 of a predefined diameter that is made of flexible plastic or another material. The cylindrical tube 20 will begin at the opening 20 located at the distal end 80 of the dildo 11 and continuing to some length to the stationary anterior wall 14 of a hollowed out chamber 15 in the dildo 11. The cylindrical tube 20 runs through the core of the dildo and is used to deliver sperm or any other type of fluid, which may also be used, from the syringe 17 and into the vagina through the dildo 11. At the stationary wall 14, the cylindrical tube 20 is attached to end of the syringe 17. The syringe 17 contains a unit of semen, or washed sperm, or any type of liquid that the user has decided to use.

Figure 2:
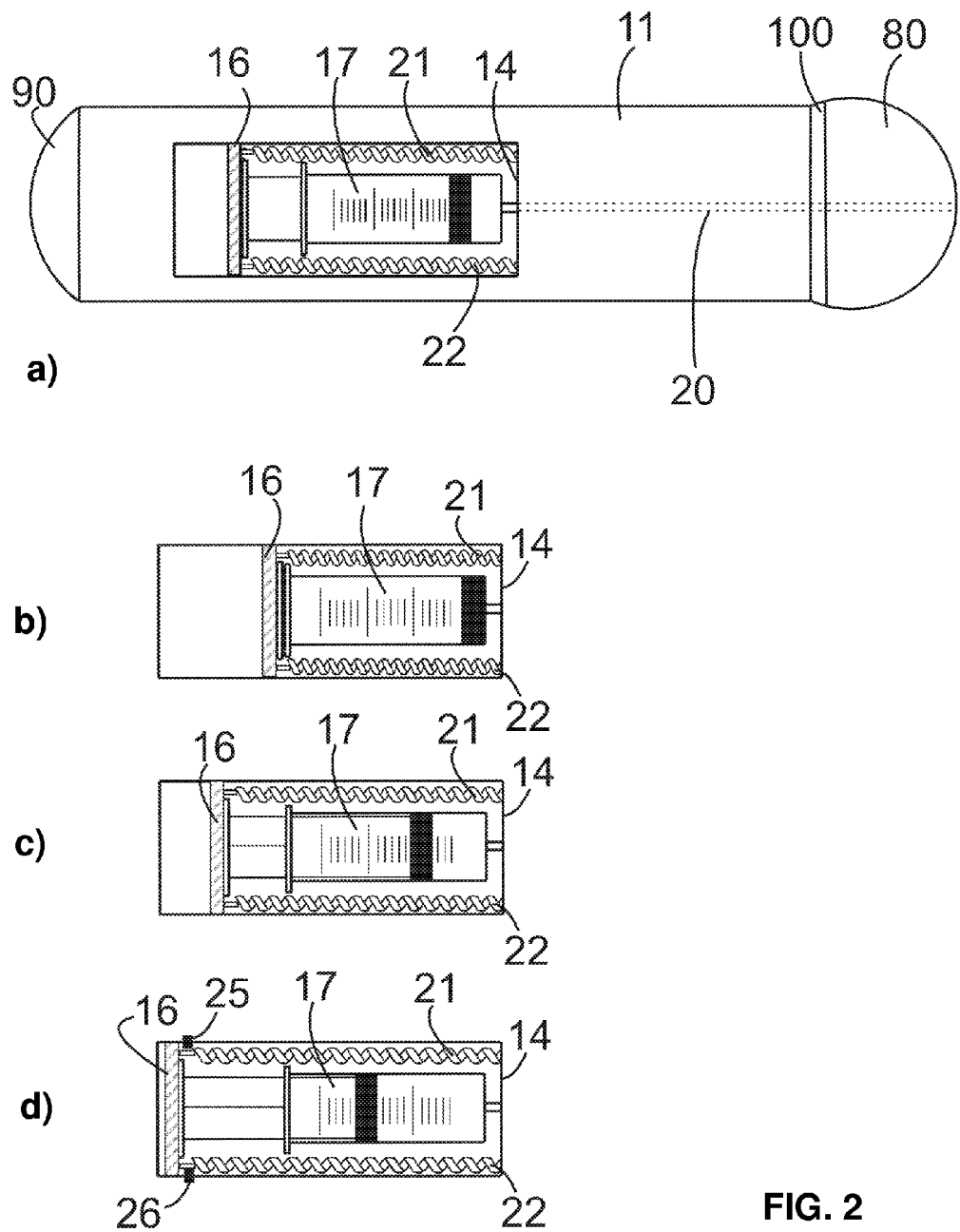
FIG. 2 shows one embodiment of the device with a spring loaded mechanism used to expel the sperm or other liquid.

For achieving the best results with ICI it is important that the sperm be delivered close or onto the cervical opening, therefore the force and velocity of the ejected sperm should be regulated as to maximize the amount of sperm that is deposited in the desired area. FIG. 2 shows an embodiment of the device with a mechanism that can be used for such a purpose. The dildo 11 contains an empty chamber 15 with a mobile wall 16 near the proximal end 90 of the dildo. The chamber 15 is made to fit a syringe 17. The movable wall 16 of the chamber is attached to springs 21-22 which are connected to the stationary wall 14 at the distal end of the chamber. When the chamber 15 is empty or when an empty syringe is placed in the chamber the mobile wall 16 is at its nearest position to the distal end and the springs 21-22 are not under tension, as shown in FIG. 2B. Placing a syringe 17 filled with sperm or any other type of liquid requires that the wall be drawn back toward the proximal end, as shown in FIG. 2C. The drawing back of the wall places the springs 21-23 under tension. FIG. 2D shows that when drawn back, the mobile wall 16 is kept in position by a mechanical pin 25-26 which can be released with a press of a button 50 located at the near proximal end 90 of the dildo 11. Release of the pins 25-26 releases the tension of the springs 21-22 and causes the mobile wall 16 to move toward the distal end 80 of the dildo 11. This action forces the plunger of the syringe 17 forward and thereby causes the release of the sperm or other liquids through the tube 20 and out of the opening 12. The tension of the springs 21-212 can be adjusted, and springs with different spring constants can be used to control the force of release of the sperm of other liquids through the opening 12.

The mechanical pin 25-26 can have a timer so that the wall 16 can be set to eject the sperm at a pre-arranged time or may be activated at will by user preference. The function of the pins 25-26 is known to someone skilled in the art and the pins 25-26 can be configured to eject sperm in a constant jet stream type of fashion or to eject in several pulses in order to simulate a physiological ejaculation. This can be done by having a series of pins with limited stopping power so that they only prevent the wall 16 from reaching the distal end for a limited time.

Figure 3:
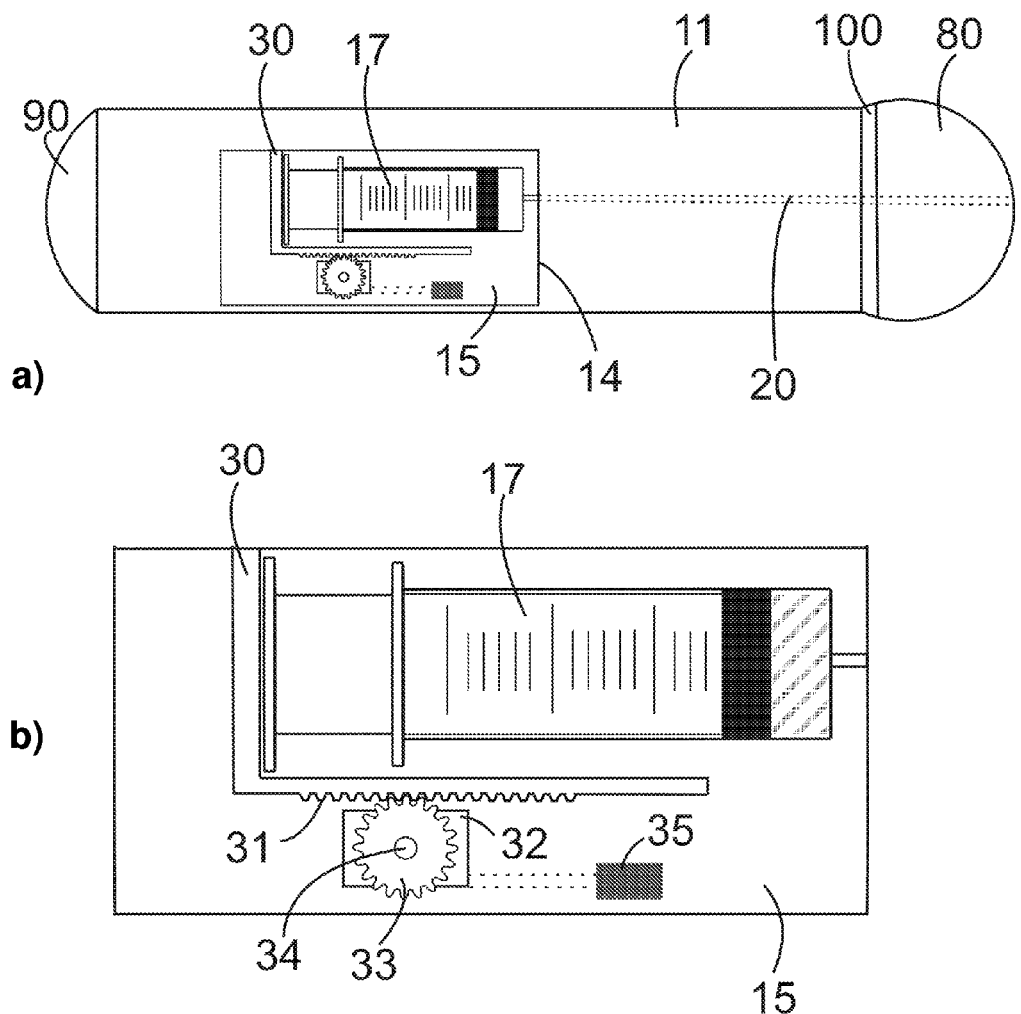
FIG. 3 shows an alternative embodiment with a syringe pump used to expel the sperm or other liquid.

An alternative embodiment of the invention uses a syringe pump, as shown in FIG. 3. The syringe pump is comprised of a motor 32, such as a stepper motor, and connected to a gear assembly 33 via a rotor 34. The gear assembly 33 is engaged with a moving wall 30 via a series of teeth 31. This rack and pinion mechanism serves to transfer the rotational energy of the motor 32 to linear movement of the moving wall 30. The moving wall 30 shown in FIG. 3 is L-shaped but other configurations of this mobile wall may be possible to one who is skilled in the art. There is also a controller 35 or a logic circuit board that is connected to the motor 32. The controller 35 is connected electronically to a panel 50 located outside the device. Operation of this embodiment begins with the user entering a command on a panel 50 outside the device. The controller 35 receives the commands from the panel 50 and begins operation of the stepper motor 32. The stepper motor 32 controls the rotation of the gear assembly 33. The rotation of the gear assembly moves the moving panel 30 towards the distal end 80. When a syringe 17 is placed inside of the chamber 15 the moving panel 30 depresses the plunger on the syringe 13. The force and velocity of the ejected sperm through the opening 16 is controlled by the instruction entered on the panel 36 outside of the device.

Figure 5:
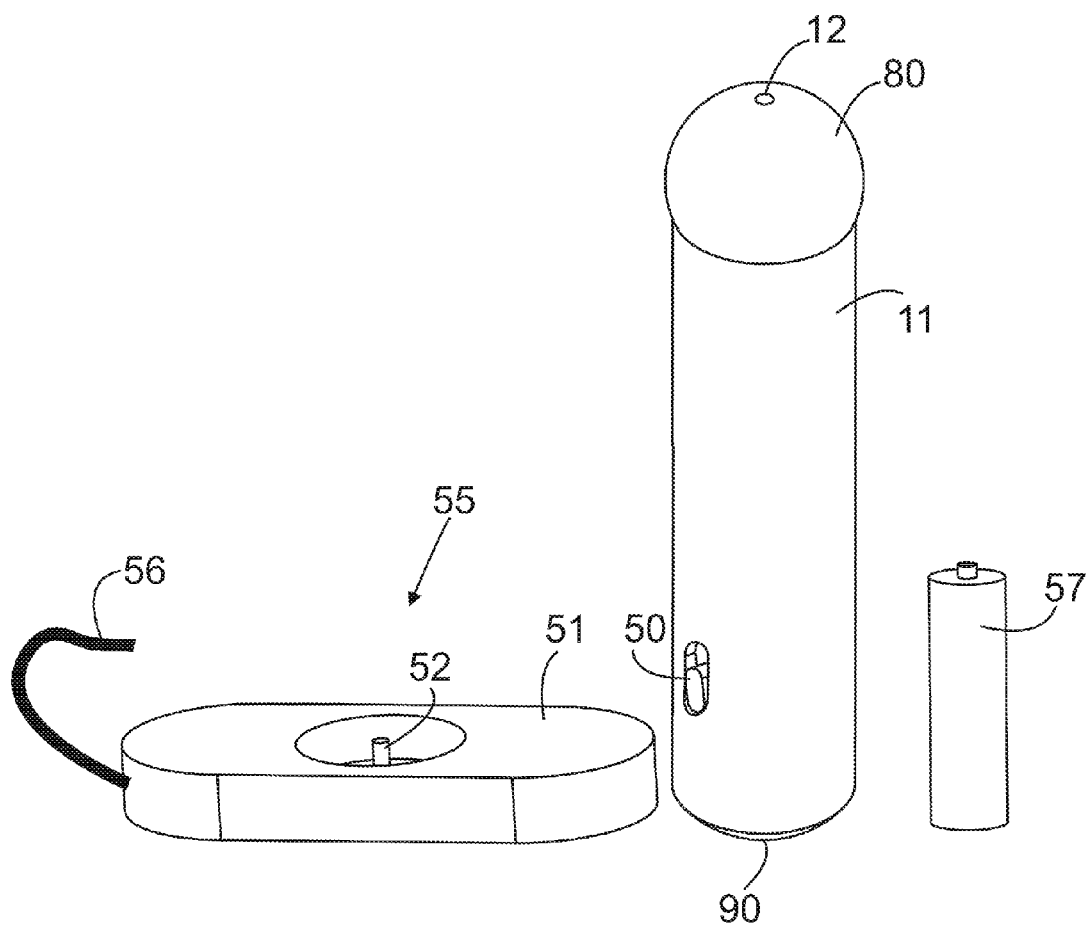
FIG. 5 shows the devices along with a battery and charger port.

Alternative embodiments can be made to increase pleasure of the user. In addition to the shape of the present device that is designed to induce pleasure, the present invention also contains a vibrating function. The vibration function is achieved by vibrating motor(s) 100 that is inserted in the distal end of the dildo 80, at its proximal end 90 or anywhere in the body of the device. In this alternative embodiment, the device can contain a panel for inserting batteries 57. The batteries 57 will be used to provide power for the vibrating motors and the stepper motor 32 for the syringe pump. Alternatively as shown in FIG. 5, the device may contain a charger 55 with a charging slot 52 in a charging base 51 with a power cord 56 that can be plugged into an electrical outlet that will provide power for recharging the batteries 57.

Figure 4:
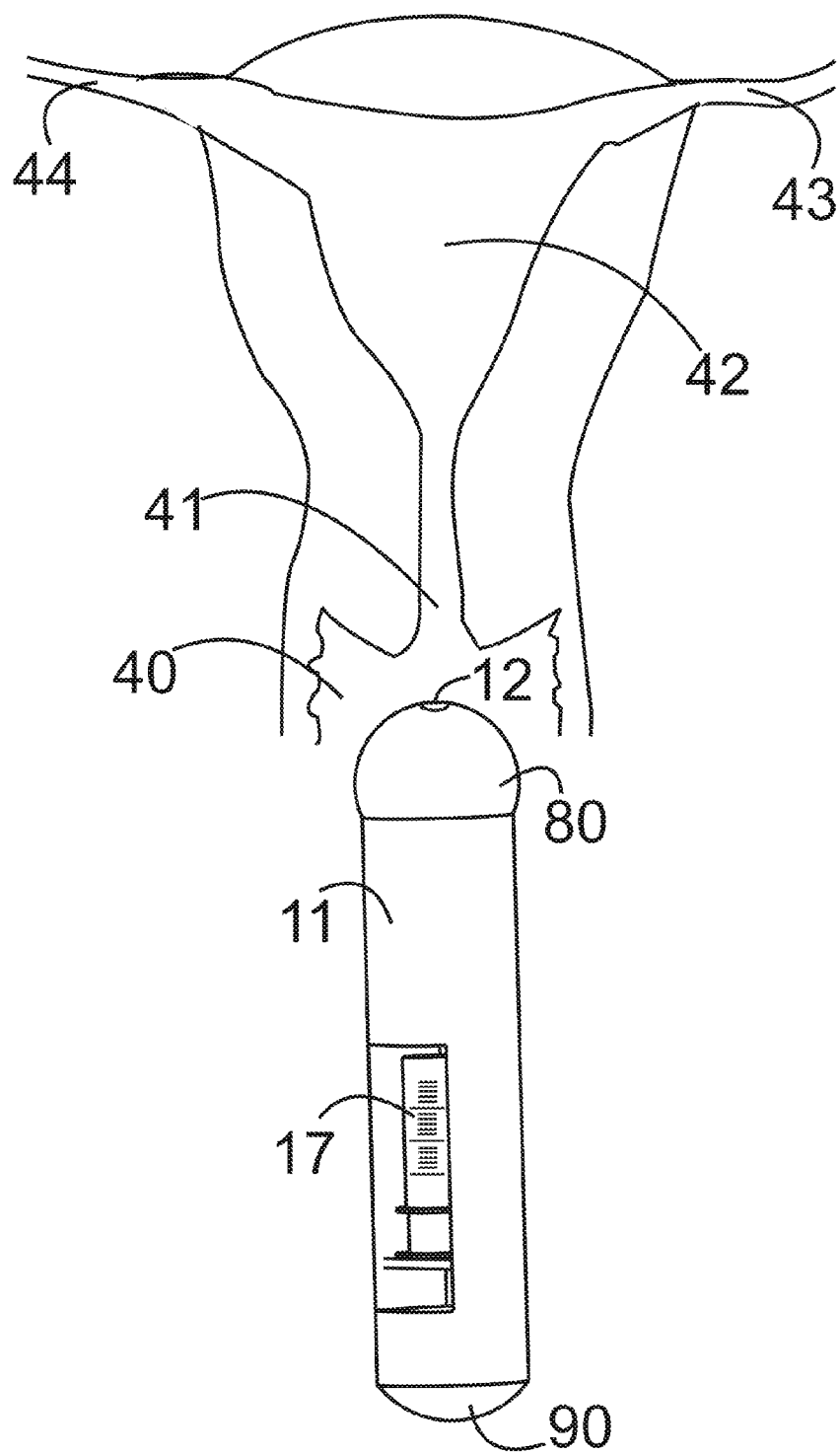
FIG. 4 shows a method for ICI using the present invention.

In all of the embodiments, as shown in FIG. 4, the device 11 is inserted into the vagina 40 and can be operated as a conventional dildo. If the device contains a vibrating motor 100 that function may be turned on in order to increase the pleasurable feelings. At the desired or prearranged time, the sperm can be ejected into the vagina 40 with the push of the button on the panel 50. The sperm then flows out of the syringe 17 through the cylindrical tube 20 in the center of the dildo 11 and is expelled out of the opening 12 in the distal end 80 of the dildo. The use of the steady stream form the syringe pump mechanism aims to ensure that the majority of the sperm arrive at or near the cervix 41. The sperm can then travel through the cervical canal 41 the uterus 42 and fallopian tubes 43-44 and attempt to fertilize an egg if there is one present. The syringe 17 also allows for ejection of the sperm through the opening 12 at the distal end 80 at a rate that is dependent on the depression of the plunger as part of the syringe 17.

The vibration function of the present invention works by having a motor 22 attached at certain points of the device. In one embodiment of the present invention, the device could contain vibrating motors 22 at the proximal 80 and distal 90 ends of the device but the motors can be placed anywhere on the device. The vibration can be turned off during the time that the sperm is ready to be ejected from the opening 12 of the device by the action of pumping mechanism or the automatic syringe pump. An optional attachment that can provide additional stimulation to the clitoris can be attached. In this manner, the device can provide pleasure and thereby attempt to induce a female orgasm after the sperm have been ejected out of the device through the opening 12. The induction of an orgasm may aid in the success of the fertility treatment.

In order to further simulate physiological sexual intercourse the device may contain a harness mount that can be attached to or is a part of the dildo 11. The harness mount can be inserted in a standard sized hole in most harnesses. The dildo 11 can then function in the same manner as previously described. Additionally, the shape of the instrument may be straight and cylindrical, it may curve near the proximal or distal ends or in the middle and may curve multiple times. The length of the object at either end of such a curve can vary. The object can also be made to vaginally enter at both proximal and distal ends with the ejecting means and chamber repeated for each end.

The chamber 15 can be designed to fit and adjust to multiple sizes and shapes of syringes. The shape of the syringe can vary in width or length, or it may be curved at some point. Alternatively, an embodiment that does not contain a syringe can be used. In this case, a tube or a cartridge may be used that is inserted in the chamber 15. In this embodiment, a plunger is provided with the device and is attached to the movable wall 16 or 30. The ejection of the sperm then proceeds as previously described with the mechanisms shown in FIG. 2 and FIG. 3.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

With respect to the above description, it is to be realized that the optimum relationships for the parts of the invention in regard to size, shape, form, materials, function and manner of operation, assembly and use are deemed readily apparent and obvious to those skilled in the art, and all equivalent relationships to those illustrated in the drawings and described in the specification are intended to be encompassed by the present invention.

What is claimed is:

1. A dildo shaped device for artificial insemination comprising:
   a. an elongated, resilient and cylindrical body having an opening at a distal end of the body;
   b. a syringe having a plunger movable along a barrel, said barrel serving as a space for storage of an element;
   c. a chamber inside said body adapted to receive said syringe, said chamber having a posterior end and an anterior end;
   d. a moving wall inside said chamber and engaged with said plunger to move said plunger from said posterior end toward the anterior end;
   e. a tube embedded inside of the body connecting said syringe to said opening at the distal end;
   f. means to move said moving wall to expel said element through said opening.

2. The dildo shaped device for artificial insemination of claim 1, wherein said means to move said moving wall comprising:
   a. a plurality of springs connected from a first end to the anterior end of said chamber and from a second end to the moving wall;
   b. a releasable pin to keep said spring under extension and keep said plunger extended,
      whereby said moving wall is moved once said pin is released, thereby rapidly expelling the element stored inside said syringe out of said opening forming a spray.

3. The dildo shaped device for artificial insemination of claim 2, wherein said plurality of springs having different spring constants to provide different moving speed to said moving wall.

4. The dildo shaped device for artificial insemination of claim 1, wherein said means to move said moving wall comprising:
   a. a motor to provide rotational power;
   b. a shaft to transfer rotational power to a gear;
   c. said gear to engage with said moving wall;
   d. a power source to provide power to said motor;
   e. said moving wall having plurality of teeth that engage with said gear, and
   f. a control circuit to control the speed of said motor and operating time of said motor,
      whereby the speed of said motor can be adjusted to expel said element in a steady stream or in the form of a spray.

5. The dildo shaped device for artificial insemination of claim 4, wherein said motor being a stepper motor with different speed settings.

6. The dildo shaped device for artificial insemination of claim 4, wherein said operating time of said motor being controlled by said control circuit.

7. The dildo shaped device for artificial insemination of claim 1, further having a vibrating motor to provide vibrational movement at the body for stimulating.

8. The dildo shaped device for artificial insemination of claim 4, wherein said power source is a rechargeable battery or an electrical outlet.

9. The dildo shaped device for artificial insemination of claim 1, wherein said device being embedded in different of dildos shapes.

10. A method to eject sperm to ensure that the majority of the sperms arrive at or near the cervix, the method comprising steps of:
   a. obtaining a dildo shaped device for artificial insemination, wherein said dildo having an opening at a distal end, a syringe embedded inside said dildo, said syringe having a plunger movable along a barrel, a tube embedded inside said dildo to connect said syringe to said opening, and means to move said plunger;
   b. filling said syringe with sperm cells;
   c. bringing said dildo in position with the user's cervix;
   d. sexually stimulating the user with said dildo, and
   e. moving said plunger to expel said sperm cells into the user when the user is stimulated,
      whereby increasing the probability of successful insemination.

11. The method of claim 10, wherein said moving the plunger step forming a steady stream of expelling sperm.

12. The method of claim 10, wherein said moving the plunger step forming a spray of expelling sperm.

* * * * *